US012041708B2

(12) United States Patent
Eisenhardt et al.

(10) Patent No.: US 12,041,708 B2
(45) Date of Patent: Jul. 16, 2024

(54) ELECTROSTATIC GROUNDING DEVICES

(71) Applicant: Desco Industries, Inc., Chino, CA (US)

(72) Inventors: Emilio Eisenhardt, Waltham, MA (US); Jeffry Brake, Lakewood, CA (US); Roberto F. Garayo, Riverside, CA (US)

(73) Assignee: Desco Industries, Inc., Chino, CA (US)

( * ) Notice: Subject to any disclaimer, the term of this patent is extended or adjusted under 35 U.S.C. 154(b) by 433 days.

(21) Appl. No.: 17/353,478

(22) Filed: Jun. 21, 2021

(65) Prior Publication Data

US 2022/0408535 A1     Dec. 22, 2022

(51) Int. Cl.
| | | |
|---|---|---|
| *H05F 3/02* | (2006.01) |
| *A43B 3/34* | (2022.01) |
| *A61B 5/00* | (2006.01) |
| *A61B 5/318* | (2021.01) |

(52) U.S. Cl.
CPC ............... *H05F 3/02* (2013.01); *A43B 3/34* (2022.01); *A61B 5/318* (2021.01); *A61B 5/6828* (2013.01); *A61B 5/6831* (2013.01)

(58) Field of Classification Search
CPC .. H05F 3/02; A43B 3/34; A61B 5/318; A61B 5/6828; A61B 5/6831
See application file for complete search history.

(56) References Cited

U.S. PATENT DOCUMENTS

| | | | |
|---|---|---|---|
| 2,933,651 A * | 4/1960 | Legge ..................... | A43B 7/36 361/220 |
| 5,184,275 A | 2/1993 | Wiegel et al. | |
| 5,576,924 A | 11/1996 | Hee | |
| 5,786,977 A | 7/1998 | Cohen | |
| 6,307,727 B1 | 10/2001 | Deangelis et al. | |
| 6,707,659 B2 | 3/2004 | Hee | |
| 2015/0223569 A1* | 8/2015 | Cox ........................ | A43C 7/00 24/712.9 |

FOREIGN PATENT DOCUMENTS

JP        6408028 B2 * 10/2018 ............... A43B 1/04

* cited by examiner

*Primary Examiner* — Scott Bauer
(74) *Attorney, Agent, or Firm* — Berkeley Law & Technology Group, LLP

(57) ABSTRACT

Embodiments of the disclosed subject matter generally relate to electrically grounding a user who may be working in an environment where static electricity might otherwise build up on the user and damage sensitive electronic devices being handled by the user. Embodiments include attaching an electrocardiogram (ECG) electrode to the user's skin and removably attaching the ECG electrode to an electrical conductor which may be detachably connected to a flexible base disposed on the outside of and under the user's shoe.

46 Claims, 9 Drawing Sheets

ELECTROSTATIC GROUNDING DEVICES

FIELD

Embodiments of the present disclosure generally relate to electrically grounding a user who may be working in an electronics factory or other environment, for example, where static electricity might otherwise build up on the user and then damage sensitive electronic devices or components being handled by the user.

INFORMATION

Persons who are involved in the manufacturing, repairing, or otherwise handling of static electricity sensitive devices, such as electronic devices or components, often wear wrist straps or specialized foot devices. They can prevent or reduce a build-up of static electricity on the bodies of these persons by providing an electrical pathway to ground. This, in turn, can protect the electronic components from static-electricity damage, and personnel from static-electricity shocks. As to the types of devices for wearing on the feet, users may wear, on the heels or toes of their shoes, strap devices that conduct the static electricity from the user to (for example) electrically conductive wax or paint on a grounded floor or mat. These devices sometimes are referred to as "foot grounders."

SUMMARY OF CERTAIN EMBODIMENTS

Broadly speaking, certain embodiments of the disclosure may relate to electrostatic grounding devices for use in dissipating static electricity that might otherwise build up or exist on the body of a user and that might otherwise damage certain sensitive electronic components being handled by the user. Embodiments include grounding devices that may be easily attached to and removed from a user's shoe, and that may be used with an electrocardiogram (ECG) electrode for placement on the user's skin. An electrical conductor may be in electrical connection with the user's body via a connection with the ECG electrode.

In a first embodiment, a grounding device may be for removable attachment to a shoe of a user and for dissipating static electricity from the user's body to a grounded surface. The shoe has a top portion, a heel portion, a left side and a right side. The grounding device further may be for use with a fastening member and an electrical conductor.

A grounding device may comprise a conductive base shaped so that, during a time that the grounding device is attached to the shoe, at least a portion of the conductive base is disposed under the shoe. The conductive base is in electrical communication with the grounded surface during a time that the shoe is on the grounded surface and the grounding device is attached to the shoe.

According to this embodiment, the fastening member may be elongated in shape and flexible and in cooperative engagement with the conductive base at at least one engagement location on the conductive base during the time that the grounding device may be attached to the shoe. The at least one engagement location may be disposed on the conductive base so that, during the time that the grounding device is attached to the shoe, the fastening member extends across the top portion of the shoe and along the left side of the shoe and the right side of the shoe and further extends in a direction toward the heel portion of the shoe.

According to this embodiment, the conductive base may grip the shoe at locations on the left and right sides of the shoe and on the heel portion of the shoe in response to a force provided by the fastening member during a time that the conductive base is cooperatively engaged with the fastening member and during the time that the grounding device is attached to the shoe. The electrical conductor may be elongated in shape and may be flexible and may provide at least part of an electrical connection between the user's body and the conductive base during a time that the electrical conductor is connected to the user's body and to the grounding device.

There are additional aspects to embodiments of the present disclosure. It should therefore be understood that the preceding is merely a brief summary of some embodiments and aspects of the present disclosure. Additional embodiments and aspects are referenced below. It should further be understood that numerous changes to the disclosed embodiments can be made without departing from the spirit or scope of the claimed subject matter. The preceding summary therefore is not meant to limit the scope of the claimed subject matter. Rather, the scope of the claimed subject matter is to be determined by appended claims and their equivalents.

BRIEF DESCRIPTION OF THE DRAWINGS

These and/or other aspects and advantages of the present disclosure will become apparent and more readily appreciated from the following description of certain embodiments, taken in conjunction with the accompanying drawings of which.

DETAILED DESCRIPTION

Figure 1:
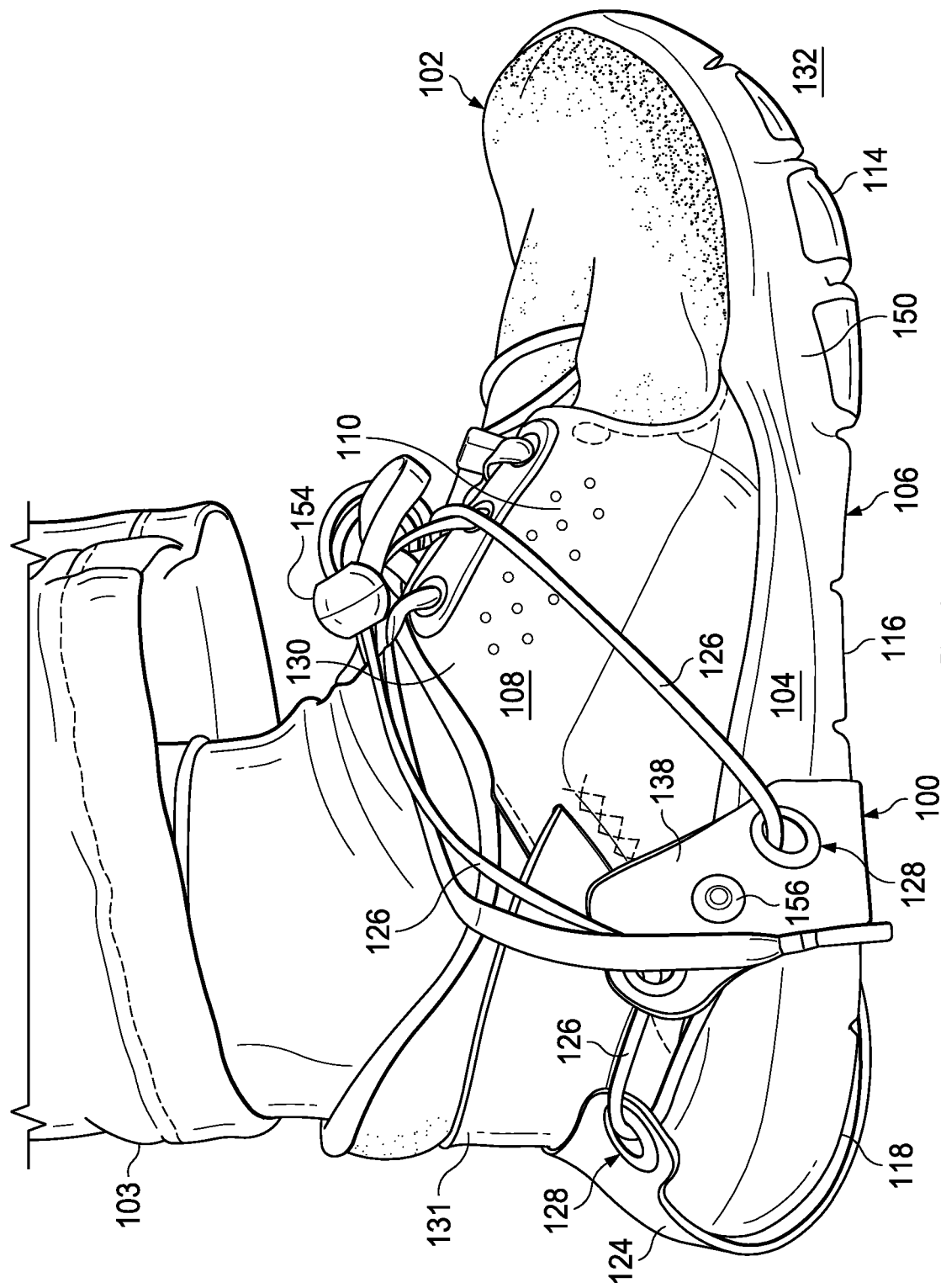
FIG. 1 is a simplified diagram of a grounding device that is attached to a shoe of a user, according to an embodiment.

The following description includes the best mode presently contemplated for carrying out claimed subject matter. Moreover, in the following description, details are set forth by way of example to enable a person of ordinary skill in the art to practice claimed subject matter without undue experimentation. Reference will be made in detail to embodiments of claimed subject matter, examples of which are illustrated in the accompanying drawings, wherein like reference numerals refer to like elements throughout. It is understood that other embodiments may be used and structural and operational changes may be made without departing from the scope of claimed subject matter.

Disclosed herein are electrostatic grounding devices for use in dissipating static electricity that might otherwise build up or exist on the body of a user and that might otherwise damage certain sensitive electronic components being handled by the user. Embodiments include grounding devices that may be easily attached to and removed from a user's shoe. Comfort may be provided to the user by use of a covering material or base constructed of rubber, vinyl or other flexible material. Moreover, in some embodiments, a single grounding device may be used for a variety of shoe sizes and designs. At least a portion of the flexible material of the base may be electrically conductive and in electrical communication with the user's body via a variety of easily attachable/detachable, electrically-conductive attachment options which electrically connect the grounding device to the user's body.

A user may select any one or more of these attachment options without having to obtain a different grounding device base. In an embodiment, attachments options may include (1) a disposable or non-disposable cord or strap for inserting inside a user's shoe and which may include a resistor, (2) a band or strap for placement around the user's leg, having a connective snap on both ends and which may include a resistor, and (3) a disposable electrode such as, for example, an ECG electrode, attached to an electrical cord or wire having a connective snap on both ends and which may include a resistor.

In an embodiment, a base may have a plurality of holes (with grommets, for example) which allows a flexible, elongated fastening member such as, for example, a strap or a shock cord, to be weaved through the holes and wrapped around the user's shoe and engage the base of the grounding device. Use of such a fastening member along with the flexible base may allow it to grip around the heel of the user's shoe and around the sides and/or top of the shoe to hold the grounding device closely to the shoe. In an embodiment, a cord lock is disposed at or near the ends of the fastening member thus allowing the user to adjust and hold the tightness of the fastening member for comfort and secure fit.

Advantages of some embodiments include providing a grounding device: that is easy both to remove from, as well as attach to, a shoe; that is adjustable to a user's shoe size and shape thus providing improved comfort; that permits a user to control the tightness of the fit of the grounding device; that is interchangeable with various types of electrically-conductive attachments for contacting a user's body and having compatible snaps or other attachment mechanisms incorporated with the base; and that may provide an improved or greater contact area with an electrically grounded surface or floor on which a user may be walking or standing. Other advantages are apparent from the descriptions below.

Figure 2:
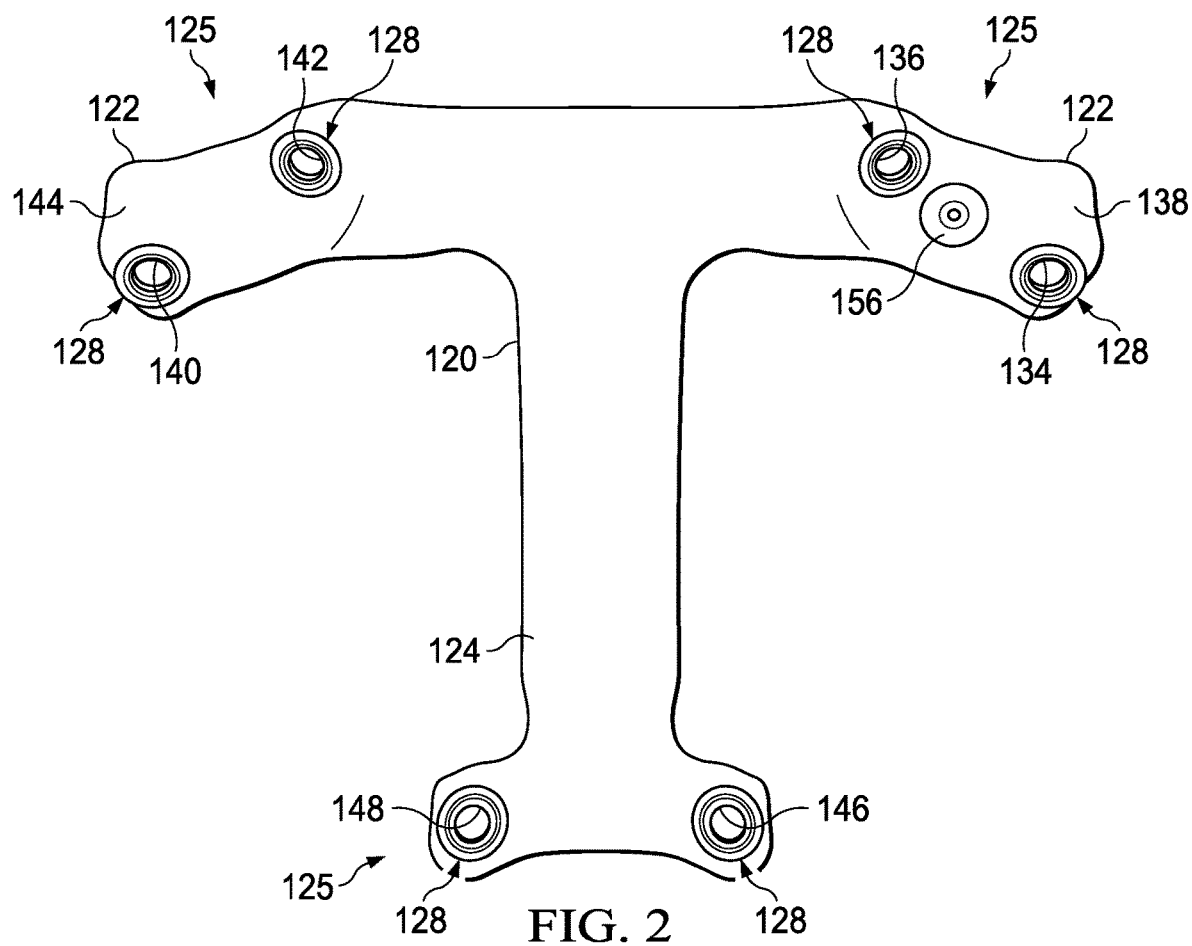
FIG. 2 depicts a plan view of features of the grounding device of FIG. 1, according to an embodiment.
Figure 3:
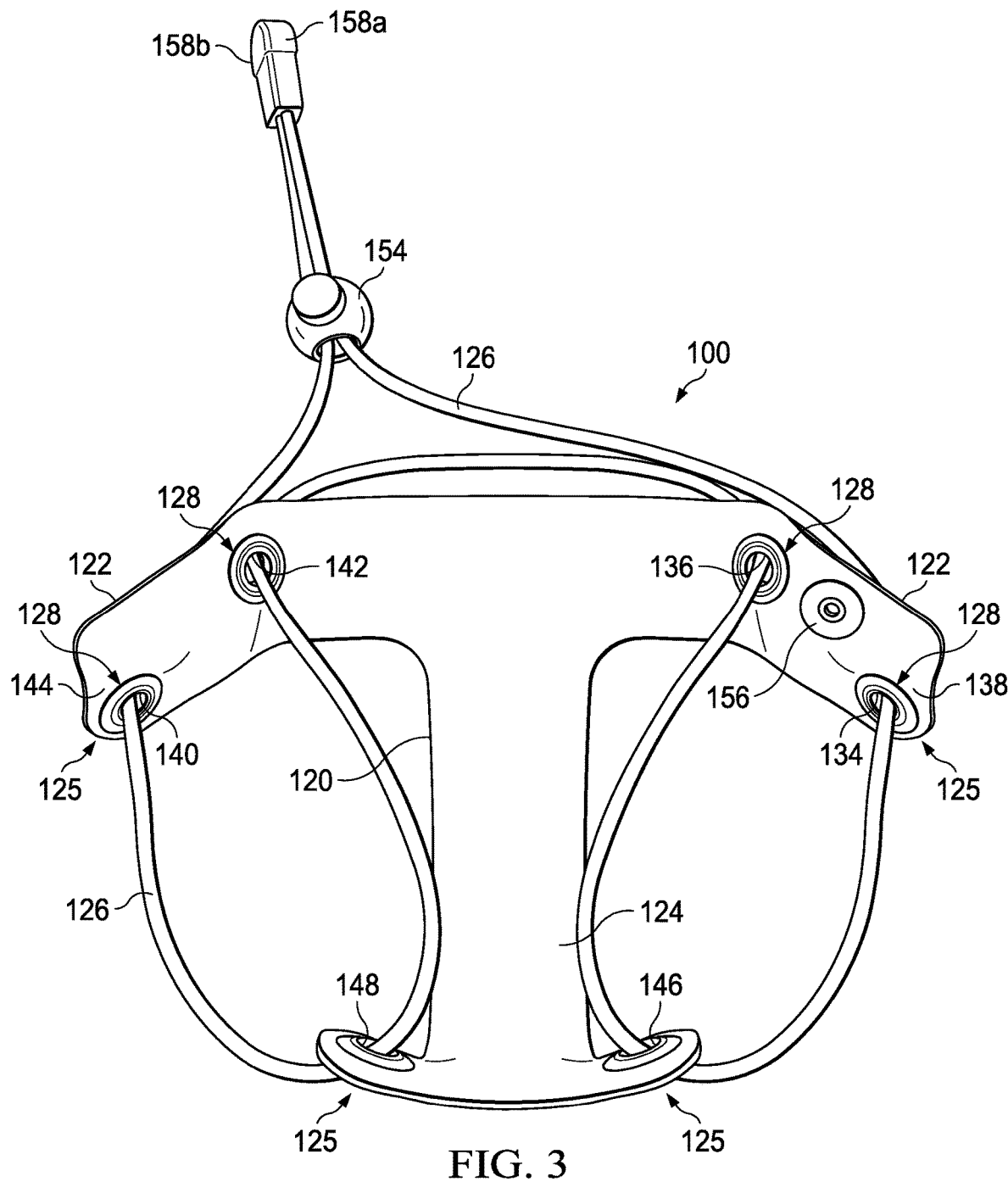
FIG. 3 is a top perspective view of features of the grounding device of FIG. 1, according to an embodiment.

FIGS. 1-3 are simplified diagrams of a grounding device 100 according to an embodiment. FIG. 1 depicts grounding device 100 that may be removably attached to a shoe 102 of a user 103. FIG. 2 depicts a base 120 of grounding device 100, along with a pair of wings 122 extending outwardly from base 120, and an elongated portion 124 extending from base 120, according to an embodiment. FIG. 3 is a top perspective view showing a fastening member 126 that is in engagement with pair of wings 122 and elongated portion 124, according to an embodiment.

Referring to FIG. 1, grounding device 100 may be removably attached to shoe 102. Shoe 102 has a midsole 104, an outsole 106, and an upper 108 comprising an upper right sidewall 110 and an upper left sidewall disposed opposite to and mirroring upper right sidewall 110, but not shown in FIG. 1 for simplicity of illustration. Upper 108 of shoe 102 may refer to a portion of shoe 102 that encloses the foot of user 103, keeping shoe 102 in place, and protecting against dirt, rocks, and moisture, etc., and that is disposed above midsole 104. Midsole 104 of shoe 102 may refer to a relatively thick layer of foam or rubber or other material disposed between upper 108 and outsole 106. Outsole 106 of shoe 102 may refer to a layer of rubber or other relatively hard or rigid material disposed on the bottom of shoe 102, and which may make contact with the ground and provide traction and durability.

Still referring to FIG. 1, outsole 106 includes a forward outsole portion 114, a middle outsole portion 116, and a rear outsole portion 118. During the times when grounding device 100 is not being worn, outsole 106 directly contacts a surface on which user 103 may be walking or standing. While shoe 102 is worn by user 103, forward outsole portion 114 may be disposed generally under the toes and the ball of the user's foot, middle outsole portion 116 may be disposed generally under an arch of the user's foot, and rear outsole portion 118 may be disposed generally under a heel of the user's foot.

Base 120 (FIG. 2) may be shaped to fit under outsole 106 of shoe 102, so that base 120 may be disposed between outsole 106 and a grounded surface 132 underlying the shoe. Grounded surface 132 may be any surface that supports some or all of the weight of the user and that is in electrical communication, directly or indirectly, with electrical ground. For example, grounded surface 132 could be a floor of a manufacturing or repair facility, where the floor is electrically grounded. As another example, grounded surface 132 could be a mat placed upon a floor, where the mat is electrically grounded.

Pair of wings 122 may extend outwardly from base 120 so that at least a portion of each wing of the pair may be positioned adjacent to midsole 104 of shoe 102, as best seen in FIG. 1. Referring to FIG. 2, elongated portion 124 may extend from base 120 in a direction generally perpendicular to pair of wings 122. At least a part of elongated portion 124 may be in contact with rear outsole portion 118 of shoe 102 as shown in FIG. 1.

Referring again to FIG. 2, base 120, pair of wings 122 and elongated portion 124 may be formed together in a generally T-shape. Such a shape may permit grounding device 100 to conform to user's shoe 102 in a snug fit manner and to have an improved or greater contact area with grounded surface 132 by having a flexible structure that can be adjusted up and down the back or rear of the user's shoe while still contacting grounded surface 132. Moreover, in an embodiment, base 120, pair of wings 122 and elongated portion 124 may be formed together as a unitary body. In alternative embodiments, however, one or more of base 120, pair of wings 122 and elongated portion 124 may be separate components that may be attached to each other and/or to one or more other components of grounding device 100.

Referring to FIG. 3, fastening member 126 may be generally elongated in shape, flexible, and may engage each wing of pair of wings 122 and elongated portion 124 at a plurality of engagement locations 125. In an embodiment, fastening member 126 may engage each wing of pair of wings 122 at a free or distal end of each wing, and further engages elongated portion 124 at at least two engagement locations 125 located at or near a free or distal end of elongated portion 124. End caps 158*a*, 158*b* are disposed at each end of fastening member 126 to prevent fraying.

Pair of wings 122 and elongated portion 124 may be flexible thereby permitting them to grip shoe 102 (as shown in FIG. 1) in response to a force provided by fastening member 126. In an embodiment, a plurality of openings 128 defined by pair of wings 122 and elongated portion 124 may be disposed at plurality of engagement locations 125. In the illustrated embodiment, plurality of openings 128 includes a plurality of grommets. Fastening member 126 may engage pair of wings 122 and elongated portion 124 by entwining pair of wings 122 and elongated portion 124 and extending through plurality of openings 128. In alternative embodiments, however, rather than holes, a plurality of engagement mechanisms may be disposed at plurality of engagement locations 125. Plurality of engagement mechanisms may have the capability of cooperatively engaging or securing fastening member 126 to pair of wings 122 and elongated portion 124. In some embodiments, plurality of engagement mechanisms may comprise one or more hooks or loops, or any combination thereof.

Thus, when one or both of the ends of fastening member 126 are pulled (by user 103, for example), the resulting force may cause pair of wings 122 and elongated portion 124 to grip shoe 102. As best shown in FIGS. 1 and 3, plurality of openings 128 may be disposed so that fastening member 126 may follow a serpentine path and extend across top portion 130 of shoe 102 and along portions of shoe's upper right sidewall 110 and upper left sidewall, and by further extending toward and looping back from rear portion 131 of shoe 102 which may be disposed at or near the heel.

In the illustrated embodiment, a path of fastening member 126 may be defined by extending through plurality of openings 128 comprising at least six openings. Plurality of openings 128 may comprise a first opening 134 and a second opening 136 defined by a right wing 138 of pair of wings 122, a third opening 142 and a fourth opening 140 defined by a left wing 144 of pair of wings 122, and a fifth opening 146 and a sixth opening 148 defined by elongated portion 124. In alternative embodiments, however, a greater or lesser number of openings may be used. Right wing 138 and left wing 144 may be disposed adjacent to right midsole 150 and left midsole, respectively, of midsole 104 of shoe 102 when grounding device 100 is attached to shoe 102.

As best seen in FIG. 3, fastening member 126 may extend through plurality of openings 128 in the following sequence: through first opening 134 of right wing 138, fifth opening 146 of elongated portion 124, second opening 136 of right wing 138, third opening 142 of left wing 144, sixth opening 148 of elongated portion 124, and fourth opening 140 of left wing 144. In alternative embodiments, however, fastening member 126 may extend through plurality of openings 128 in different sequences and following alternative paths. It is appreciated that the above use of the terms "first", "second", "third", etc., is a common patent-language convention to distinguish between repeated instances of an element or limitation. These terms are to distinguish different elements of an embodiment or claim, and are not terms intended to supply a numerical limit, and are not terms intended to indicate that elements, limitations or actions must appear or be performed in that order. Thus, for example, the above phrase "fourth opening 140 of left wing 144" is not intended to suggest that this one wing must have a total of four or more openings. Rather, this usage of "fourth," for example, is intended merely to distinguish a specific opening, simply being referred to as "fourth opening," from other illustrated openings in grounding device 100, as shown in FIGS. 1-3.

In an embodiment, a single pull on or near one or both ends of fastening member 126 may cause base 120, pair of wings 122 and elongated portion 124 to simultaneously snug or tighten onto shoe 102. Moreover, in an embodiment, base 120, pair of wings 122 and/or elongated portion 124 may have dimensions and may be constructed in whole or in part, of a flexible material (e.g., rubber or vinyl), so that a single grounding device may accommodate a range of shoe sizes and designs, thus reducing the size of an inventory of grounding devices that might otherwise be required for a plurality of persons working at the same location.

In an embodiment, fastening member 126 may be constructed of an elastic material permitting an extension of the length of fastening member in response to an external longitudinal force or a pulling force applied to one or more ends of fastening member 126 (such as a force being applied by user 103, for example), and further permitting a retraction in the length of fastening member 126 in response to a release of the pulling force. In an embodiment, fastening member 126 may comprise a shock cord (sometimes also referred to as a bungee cord). In yet another embodiment, while fastening member 126 may be flexible, it also may be non-elastic, thus not materially stretching or extending in length in response to the longitudinal or pulling force. In various embodiments, fastening member 126 may comprise a strap, a strand, a rope, a lace, a cord, a string, a band, a ribbon, a wire, and/or a line. Moreover, while fastening member 126 of FIGS. 1 and 3 comprises a single, continuous member, alternative embodiments may include a fastening member comprising a plurality of members that may be connected or otherwise cooperatively engaged with one another.

Referring again to FIGS. 1 and 3, a clamping mechanism 154 may secure fastening member 126 at plurality of engagement locations 125 while retaining the force resulting from the pulling of fastening member 126. Thus, this force may be retained or held when user 103 no longer may be gripping or pulling fastening member 126. Both ends of fastening member 126 may extend through clamping mechanism 154. In an embodiment, a spring loaded member (not shown) internal to clamping mechanism 154 may press down upon both ends when it is desired to secure clamping mechanism 154 in a closed or locked position without the need to tie a knot in fastening member 126. Thus, clamping mechanism 154 may selectively permit fastening member 126 to slide through clamping mechanism 154 when it is unlocked or opened, or to prevent movement through clamping mechanism 154 when it is locked or closed. In an embodiment, clamping mechanism 154 may comprise a cord lock. Cord locks may sometimes be referred to as cord fasteners, plastic stoppers, spring clasps or cord toggles. In addition to cord locks, other types of clamping mechanisms for securing fastener member 126 and retaining the external force may include cord stoppers, latches, magnetic clamps, and hose clamps.

In an embodiment, base 120, elongated portion 124, or at least one wing of pair of wings 122, or any combination thereof, may be constructed, in whole or in part, of a flexible material having electrically conductive properties. These conductive properties may provide at least part of an electrical pathway so that an electrical charge may flow from user 103 to conductive surface 132 underlying shoe 102 via grounding device 100, as described in more detail elsewhere herein. In an embodiment, base 120, elongated portion 124, and pair of wings 122 all may be constructed of flexible rubber, at least portions of which may include laminated layers. An inside laminate layer (e.g., the layer that is in direct contact with shoe 102) may include portions that are not conductive to electricity, and the outside or opposite laminate layer may include portions that are infused with carbon particles thereby making these portions conductive to electricity. However, the foregoing is only an example; other embodiments may include other constructions that provide material flexibility and electrical conductivity to provide at least part of the electrical pathway described herein.

As can be appreciated, certain of the above described features of grounding device 100 of FIGS. 1-3 allow for easy attachment to and removal from user's shoe 102. Moreover, certain of these features permit grounding device 100 to be adjustable so as to fit various shoe sizes and designs and to allow user 103 to control the tightness of the fit, thus improving comfort.

Although not shown in FIGS. 1-3, but as shown and discussed in more detail elsewhere herein, at least part of an electrical pathway or connection between user 103 and grounding device 100 may be provided by an electrical conductor which may be flexible and elongated in shape. In some embodiments, electrical conductor may include a resistor which may reduce or eliminate pain or injury to user 103 caused by a discharge of static electricity. In an embodiment, a first end of the electrical conductor may be connected to or in direct contact with user's body (e.g., by directly touching the user's skin or touching the clothing fabric that in turn is directly touching the skin) and a second end may be connected to base 120, elongated portion 124, or at least one wing of pair of wings 122. When grounding device 100 is in contact with a grounded surface, such as, for example, a grounded floor of a building or a grounded mat disposed on the building's floor, any static electrical charge that might otherwise build up or exist on user's body, may instead flow from user's body through the electrical conductor, through grounding device 100 (which is attached to user's shoe 102) and to electrical ground via grounded surface 132.

In an embodiment, the first end of the electrical conductor may be connected to user's body via an electrical connection to an ECG electrode which may be disposable and may be placed upon or attached to user's skin. In an alternative embodiment, the first end of the electrical conductor may be connected to user's body via a band or strap which may be placed in contact with and secured to the skin of the user's leg, by being worn about the leg, for example. In an embodiment, this band may be made of an elastic fabric for easily conforming to the user's leg and may include an electrically conductive material inserted within the band which touches the skin of the user's leg.

In yet another embodiment, the electrical conductor may comprise a conductive strand or strap having a first end which may be placed within the user's shoe so that the electric charge may flow from the user's foot to the conductive strap. To achieve this, conductive strap may be placed between the inside of shoe 102 and a sock of user 103, or alternatively, may be placed inside both shoe 102 and the sock, so that the conductive strap may directly contact the skin of user's foot. In an embodiment, conductive strap may be constructed of a fabric such as, for example, polyester, and may include a metallic thread or an electrically conductive elastomer. In other embodiments, however, other materials may be used that provide for flexibility, comfort and electrical conductivity.

In an embodiment, the second end of the electrical conductor may be detachably connected to grounding device 100. In order to detachably connect the second end of the electrical conductor to grounding device 100 at an attachment location, an electrically conductive connector may be used. In the embodiment of FIGS. 2 and 3, an electrically conductive metal snap 156 disposed on right wing 138 may be used for connecting the electrical conductor to grounding device 100. However, other types of connectors may be used as well such as, for example, (a) a banana jack, (b) a polymer snap, (c) a buckle, (d) a D-ring, or (e) a snap hook. Such connectors may permit the electrical charge to flow from the electrical conductor to base 120, elongated portion 124, or at least one wing of pair of wings 122, or some other location of grounding device 100.

As can be seen, the use of such connectors may advantageously provide users with an option to easily change the type of component for connecting to or abutting user's body, without the necessity of locating and donning a different grounding device. Although the illustrated embodiment shows an attachment location on right wing 138, alternative embodiments may include other attachment locations located on base 120, elongated portion 124, or left wing 144, wherein said alternative locations may have the conductive properties described above, so that the electrical charge may flow from the electrical conductor through the alternative attachment location, to base 120, elongated portion 124, or left wing 144, and to electrical ground.

Figure 4:
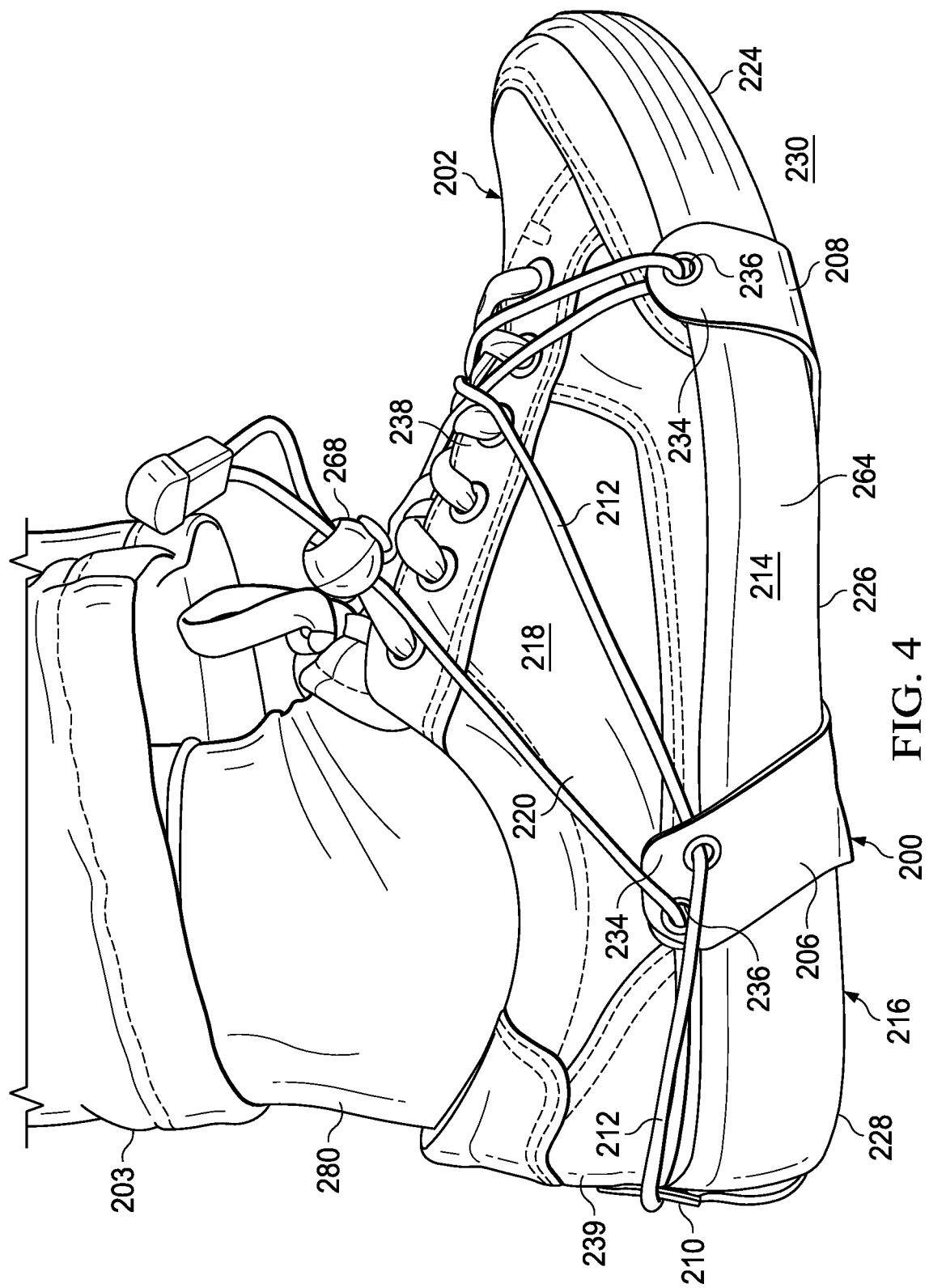
FIG. 4 is a simplified diagram of a grounding device that is attachable to a shoe of a user, according to an alternative embodiment.
Figure 5:
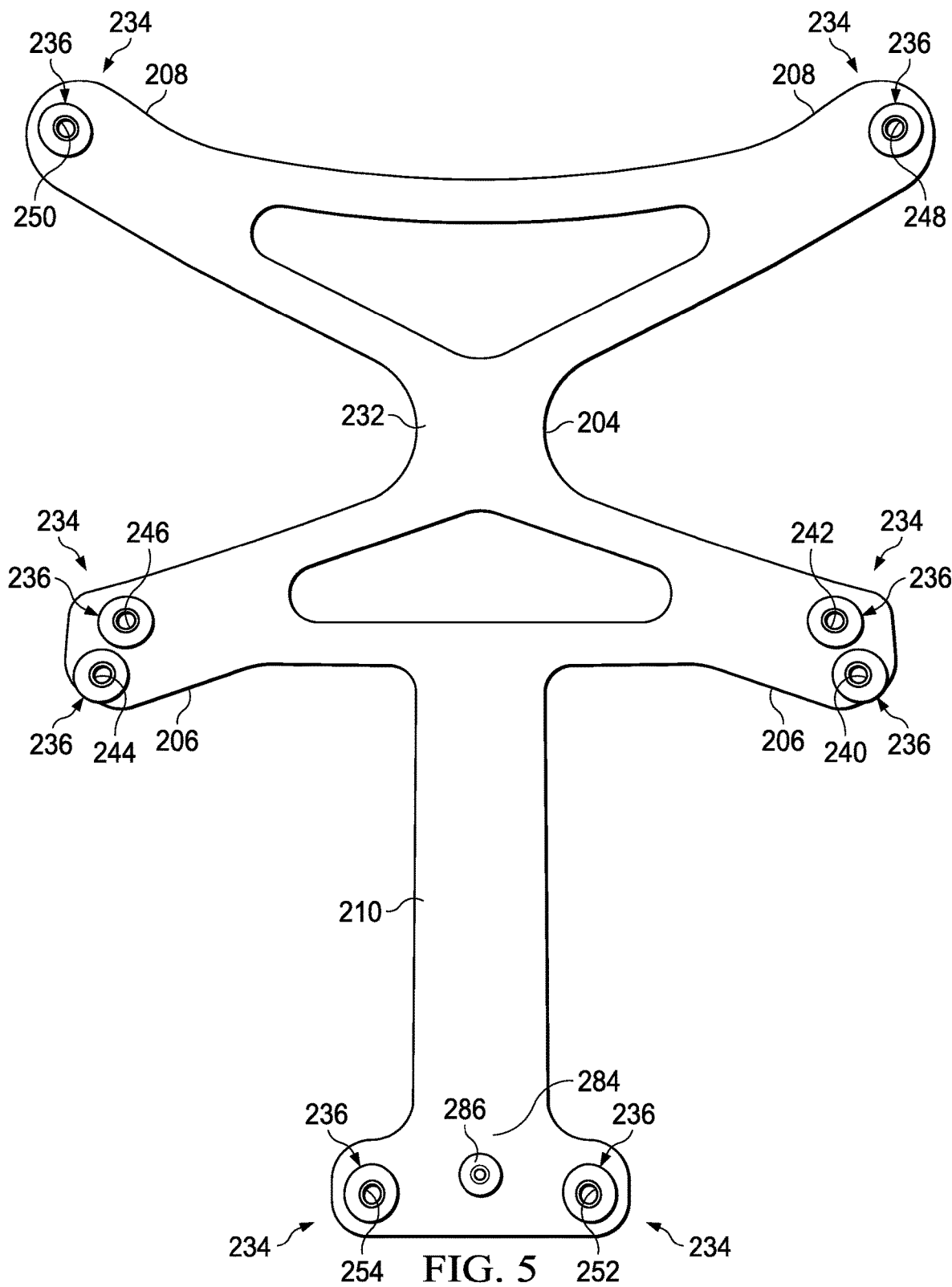
FIG. 5 depicts a plan view of features of the grounding device of FIG. 4, according to an embodiment.
Figure 6:
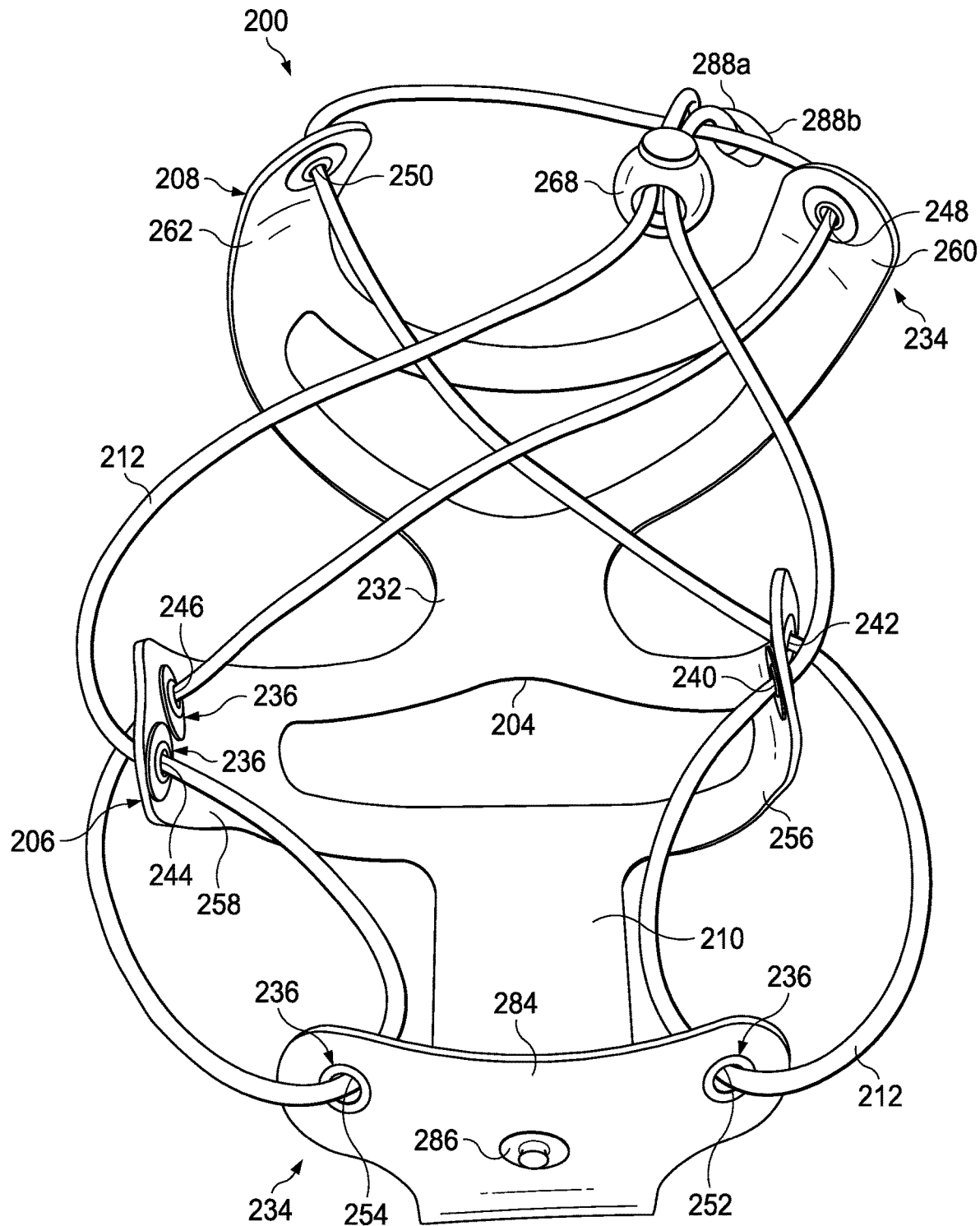
FIG. 6 is a top perspective view of features of the grounding device of FIG. 4, according to an embodiment.

FIGS. 4-6 are simplified diagrams of a grounding device 200 according to an alternative embodiment. FIG. 4 depicts grounding device 200 as attached to a shoe 202 of a user 203. FIG. 5 is a plan view depicting a base 204 of grounding device 200, along with a first pair of wings 206 extending outwardly from base 204 and a second pair of wings 208 extending outwardly from base 204 and spaced apart from first pair of wings 206. Also shown is an elongated portion 210 extending from base 204 in a direction generally perpendicular to first and second pairs of wings 206, 208.

Each pair of first and second pairs of wings 206, 208 may be angled away from one another, whereby second pair of wings 208 may be angled in a generally forward direction, and first pair of wings 206 may be angled in a generally rearward direction. In alternative embodiments, however, first and second pairs of wings, 206, 208 may have different angle orientations, including having a parallel orientation. FIG. 6 is a top perspective view showing a fastening member 212 that is in engagement with first and second pairs of wings 206, 208 and elongated portion 210.

Referring to FIG. 4, grounding device 200 may be removably attached to shoe 202. Shoe 202 has a midsole 214 an outsole 216, and an upper 218 comprising an upper right sidewall 220 and an upper left sidewall which is disposed opposite to and mirrors upper right sidewall 220, but is not shown in FIG. 4 for simplicity of illustration. Outsole 216 includes a forward outsole portion 224, a middle outsole portion 226, and a rear outsole portion 228. When shoe 202 is worn by user 203, forward outsole portion 224 may be disposed generally under the toes and/or ball of user's foot, middle outsole portion 226 may be disposed generally under the arch of user's foot, and rear outsole portion 228 may be disposed generally under the heel of the user's foot.

Base 204 may be shaped to fit under outsole 216 of shoe 202, so that base 204 is disposed between outsole 216 and a grounded surface 230 underlying shoe 202. Grounded surface 230 may be any surface that supports some or all of the weight of user and that is in electrical communication, directly or indirectly, with electrical ground. For example, grounded surface 230 could be a floor of a manufacturing or repair facility, where the floor is electrically grounded. As another example, grounded surface 230 could be an electrically grounded mat placed upon a floor.

First and second pairs of wings 206, 208 may extend outwardly from base 204 so that at least a portion of each wing of first and second pairs 206, 208 may be positioned adjacent to midsole 214 of shoe 202 as best seen in FIG. 4. As best seen in FIG. 5, elongated portion 210 extends rearwardly from base 204 in an orientation that may be generally perpendicular to first and second pairs of wings 206, 208. At least a part of elongated portion 210 may be in contact with rear outsole portion 228 of shoe 202.

Referring to FIG. 5, base 204 may include a spacer portion 232 disposed so that second pair of wings 208 may be spaced apart from first pair of wings 206 by spacer portion 232. Spacer portion 232 may be further disposed so that it generally is in contact with middle outsole portion 226 of outsole 216 of shoe 202 when grounding device 200 is removably attached to shoe 202. Accordingly, base 204, first and second pairs of wings 206, 208, spacer portion 232 and elongated portion 210 may form a shape or geometry that may permit grounding device 200 to conform well to user's shoe 202 and to have an improved or greater contact area with grounded surface 230 by having a flexible structure that can be adjusted up and down the back of user's shoe while still contacting grounded surface 230. Moreover, base 204, first and second pairs of wings 206, 208, spacer portion 232, and elongated portion 210 may be formed or constructed together as a unitary body. In alternative embodiments, however, one or more of base 204, first and second pairs of wings 206, 208, spacer portion 232, and elongated portion 210 may be separate components that may be attached to each other and/or to one or more other components of grounding device 200.

Referring to FIG. 6, fastening member 212 may be generally elongated in shape, flexible, and may engage each wing of first and second pairs of wings 206, 208 and elongated portion 210 by entwining elongated portion 210 and each wing of first and second pairs of wings 206, 208 at a plurality of engagement locations 234 (FIG. 5). In an embodiment, fastening member 212 engages each wing of first and second pairs of wings 206, 208 at a free or distal end of each wing, and further engages elongated portion 210 at at least two engagement locations 234 disposed at a free or distal end of elongated portion 210. End caps 288a, 288b are disposed at each end of fastening member 212 to prevent fraying.

First and second pairs of wings 206, 208 and elongated portion 210 may be flexible thereby permitting them to grip shoe 202 (as shown in FIG. 4) in response to a force provided by the fastening member 212. In the illustrated embodiment, a plurality of openings 236 having grommets are defined by first and second pairs of wings 206, 208 and elongated portion 210 and may be disposed at plurality of engagement locations 234. Fastening member 212 may engage first and second pairs of wings 206, 208 and elongated portion 210 by extending through plurality of openings 236. In alternative embodiments, however, rather than holes, a plurality of engagement mechanisms may be disposed at engagement locations 234. Engagement mechanisms may have the capability of cooperatively engaging or securing fastening member 212 to first and second pairs of wings 206, 208 and elongated portion 210. In some embodiments, engagement mechanisms may comprise one or more hooks, or loops, or any combination thereof.

When one or both of the ends of fastening member 212 are pulled (by user 203, for example), the resulting force may cause first and second pairs of wings 206, 208 and elongated portion 210 to grip shoe 202. As best seen in FIGS. 4 and 6, plurality of openings 236 may be disposed so that fastening member 212 may follow a serpentine path and extend across a top portion 238 of shoe 202 and along the shoe's upper right sidewall 220 and upper left sidewall, and further extend toward and loop back from rear portion 239 of shoe 202 which may be disposed at or near the heel.

In the illustrated embodiment, path of fastening member 212 may be defined, at least in part, by extending through plurality of openings 236, which may comprise at least eight openings. Thus, plurality of openings 236 may comprise a first opening 240 and a second opening 242 defined by a right first wing 256 of first pair of wings 206, a third opening 244 and a fourth opening 246 defined by a left first wing 258 of first pair of wings 206, a fifth opening 248 defined by a right second wing 260 of second pair of wings 208, a sixth opening 250 defined by a left second wing 262 of second pair of wings 208, and a seventh opening 252 and an eighth opening 254 defined by elongated portion 210. When grounding device 200 is attached to shoe 202, right first wing 256 and right second wing 260 may be disposed adjacent to a right side 264 of midsole 214 of shoe 202, and left first wing 258 and left second wing 262 may be disposed adjacent to a left side of midsole 214 which such side is disposed opposite to and mirrors right side 264, but which is not shown in FIG. 4 for simplicity of illustration.

According to an embodiment, as best seen in FIG. 6, fastening member 212 may extend through plurality of openings 236 in the following sequence: through first opening 240 of right first wing 256, seventh opening 252 of elongated portion 210, second opening 242 of right first wing 256, sixth opening 250 of left second wing 262, fifth opening 248 of right second wing 260, fourth opening 246 of left first wing 258, eighth opening 254 of elongated portion 210, and third opening 244 of left first wing 258. In alternative embodiments, however, fastening member 212 may extend through plurality of openings 236 in different sequences and following alternative paths.

As previously mentioned, it is appreciated that the above use of the terms "first", "second", "third", etc., is a common patent-language convention to distinguish between repeated instances of an element or limitation. These terms are to distinguish different elements of an embodiment or claim, and are not terms intended to supply a numerical limit, and are not terms intended to indicate that elements, limitations or actions must appear or be performed in that order. Thus, for example, the above phrase "fourth opening 246 of left first wing 258" is not intended to suggest that this one wing has a total of four or more openings. Rather, this usage of "fourth," for example, is intended merely to distinguish a specific opening, simply being referred to as "fourth opening," from other illustrated openings in grounding device 200, as shown in FIGS. 4-6.

Again, the above may describe path of fastening member 212 in the illustrated embodiment. However, alternative embodiments may include other fastening member 212 paths or sequences for engaging first and second pairs of wings 206, 208 and elongated portion 210 in order to enable them to grip shoe 202 in response to the force provided by fastening member 212. Also, alternative embodiments may employ a greater or lesser number of openings than those shown in the illustrated embodiments. As a non-limiting example, rather than right and left first wings 256, 258 each defining two holes as shown in FIGS. 5-6, in an alternative embodiment, right and left first wings 256, 258 may each define only one hole through which fastening member 212 may pass twice.

In an embodiment, a single pull on or near one or both ends of fastening member 212 may cause base 204, first and second pairs of wings 206, 208 and elongated portion 210 all to simultaneously snug or tighten onto shoe 202. Moreover, in an embodiment, base 204, first and second pairs of wings 206, 208 and/or elongated portion 210 may have dimensions and may be constructed in whole or in part, of a flexible material (e.g., rubber or vinyl), so that a single grounding device may accommodate a range of shoe sizes and designs, thus reducing the size of an inventory of grounding devices that might otherwise be required for a plurality of persons working at the same location. In alternative embodiments, however, there may be included other constructions and geometries that provide material flexibility as well as provide electrical conductivity. As a non-limiting example, other embodiments may include foot grounding devices not having one or more pairs of wings. Nevertheless, such alternative grounding devices may comprise a flexible material adapted to grip a user's shoe (at the heel and at one or more portions of the shoe forward of the heel) in response to a force of one or more flexible fastening members that entwine the grounding device.

In an embodiment, fastening member 212 may be constructed of an elastic material permitting an extension of its length in response to an external longitudinal force or a pulling force applied on or near one or more of its ends (such as a pulling force being applied by user 203, for example), and further permitting a retraction or reduction in fastening member's 212 length in response to a release of the longitudinal or pulling force. In an embodiment, fastening member 212 may comprise a shock cord (sometimes also referred to as a bungee cord). In yet another embodiment, while fastening member 212 may be flexible, it also may be non-elastic, thus not materially stretching or extending in length in response to the longitudinal or pulling force. In various embodiments, fastening member 212 may comprise a strap, a strand, a rope, a lace, a cord, a string, a band, a ribbon, a wire, and/or a line. Moreover, while fastening member 212 of FIGS. 4 and 6 comprises a single continuous member, alternative embodiments may include a fastening member comprising a plurality of members that may be cooperatively engaged with or connected to one another.

Referring again to FIG. 4, a clamping mechanism 268 may secure fastening member 212 to elongated portion 210 and first and second pairs of wings 206, 208 while retaining a force resulting from the pulling of fastening member 212. Thus, for example, this force may be retained or held when user 203 no longer may be holding or pulling fastening member 212. In an embodiment, both ends of fastening member 212 may extend through clamping mechanism 268, whereupon a spring loaded member (not shown) internal to clamping mechanism 268 may press down upon both ends when it is desired to place clamping mechanism 268 in a closed or locked condition without a need to tie a knot in fastening member 212. In an embodiment, clamping mechanism 268 may selectively permit fastening member 212 to slide through clamping mechanism 268 when it is in an unlocked or opened condition or to prevent movement through clamping mechanism 268 when it is in a locked or closed condition. In an embodiment, clamping mechanism 268 may comprise a cord lock. Cord locks may sometimes be referred to as cord fasteners, plastic stoppers, spring clasps or cord toggles. In addition to cord locks, other types of clamping mechanisms for securing fastening member 212 and retaining the external force may include cord stoppers, latches, magnetic clamps, and hose clamps.

In an embodiment, base 204, one or more wings of first and second pairs of wings 206, 208, or elongated portion 210 (or any combination thereof) may be constructed, in whole or in part, of a flexible material having electrically-conductive properties. These conductive properties may permit at least part of an electrical pathway to exist so that an electrical charge may flow from user 203 to conductive surface 230 underlying shoe 202 via grounding device 200, as described in more detail elsewhere herein. In an embodiment, base 204, elongated portion 210, spacer portion 232, and first and second pairs of wings 206, 208 all are constructed of flexible rubber, wherein at least portions of which include laminated layers. An inside laminate layer (referring to the layer that is in direct contact with shoe 202) may include portions that are not conductive to electricity, and the outside or opposite laminate layer may include portions that may be infused with carbon particles thereby making these portions conductive to electricity. However, the foregoing is only an example; other embodiments may include other constructions that provide material flexibility as well as provide electrical conductivity to permit the at least part of the electrical pathway described herein.

As can be appreciated, certain of the above described features of grounding device 200 of FIGS. 4-6 may allow for easy attachment to, and removal from, user's shoe 202. Moreover, certain of these features may permit grounding device 100 to be adjustable so as to fit various shoe sizes and designs and to allow user to control the tightness of the fit, thus improving user comfort.

Figure 7:
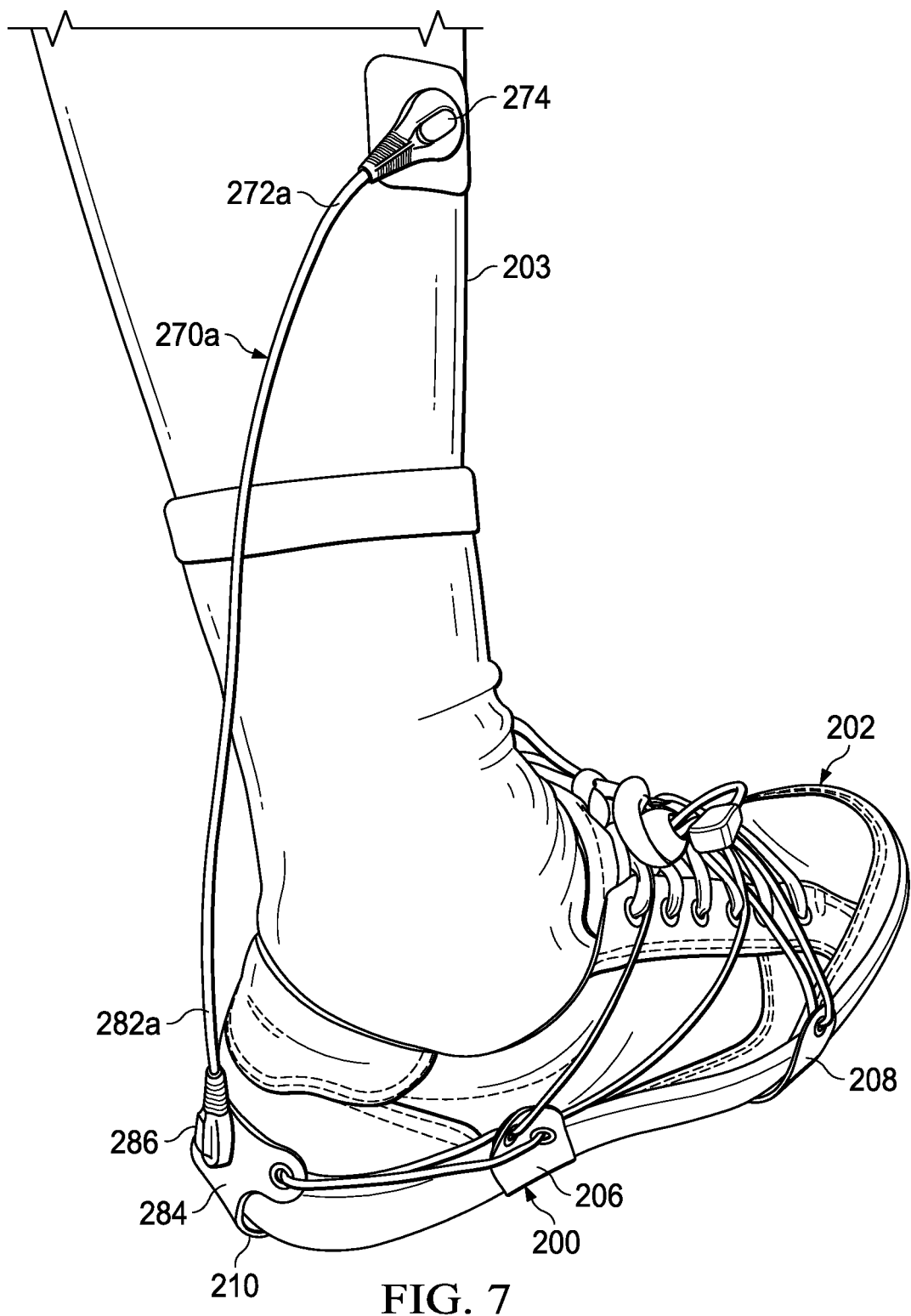
FIG. 7 depicts an electrical conductor connected to a user's body via an ECG electrode, according to an embodiment.
Figure 8:
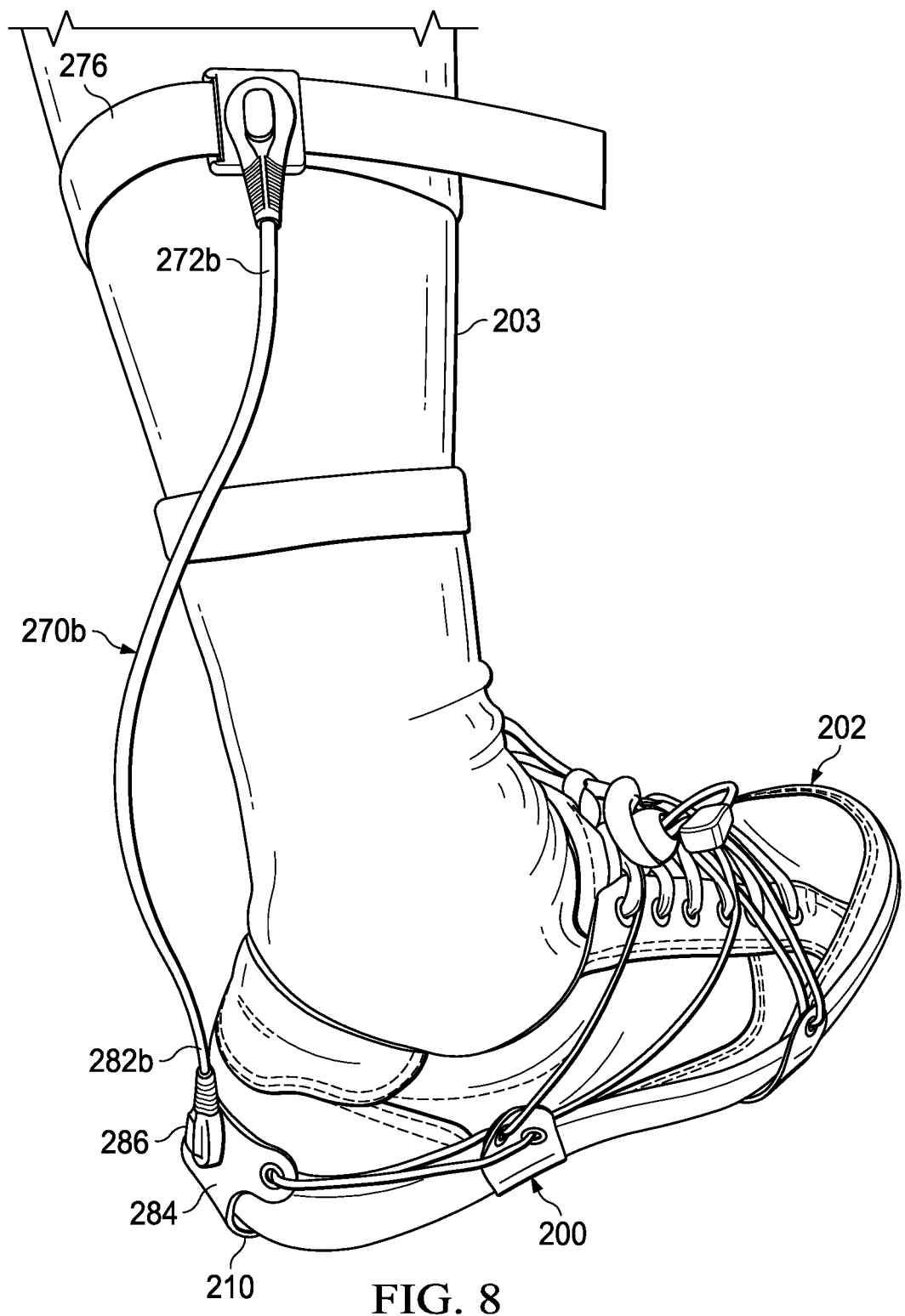
FIG. 8 depicts an electrical conductor connected to a user's body via a band or strap in contact with a user's leg, according to an embodiment.
Figure 9:
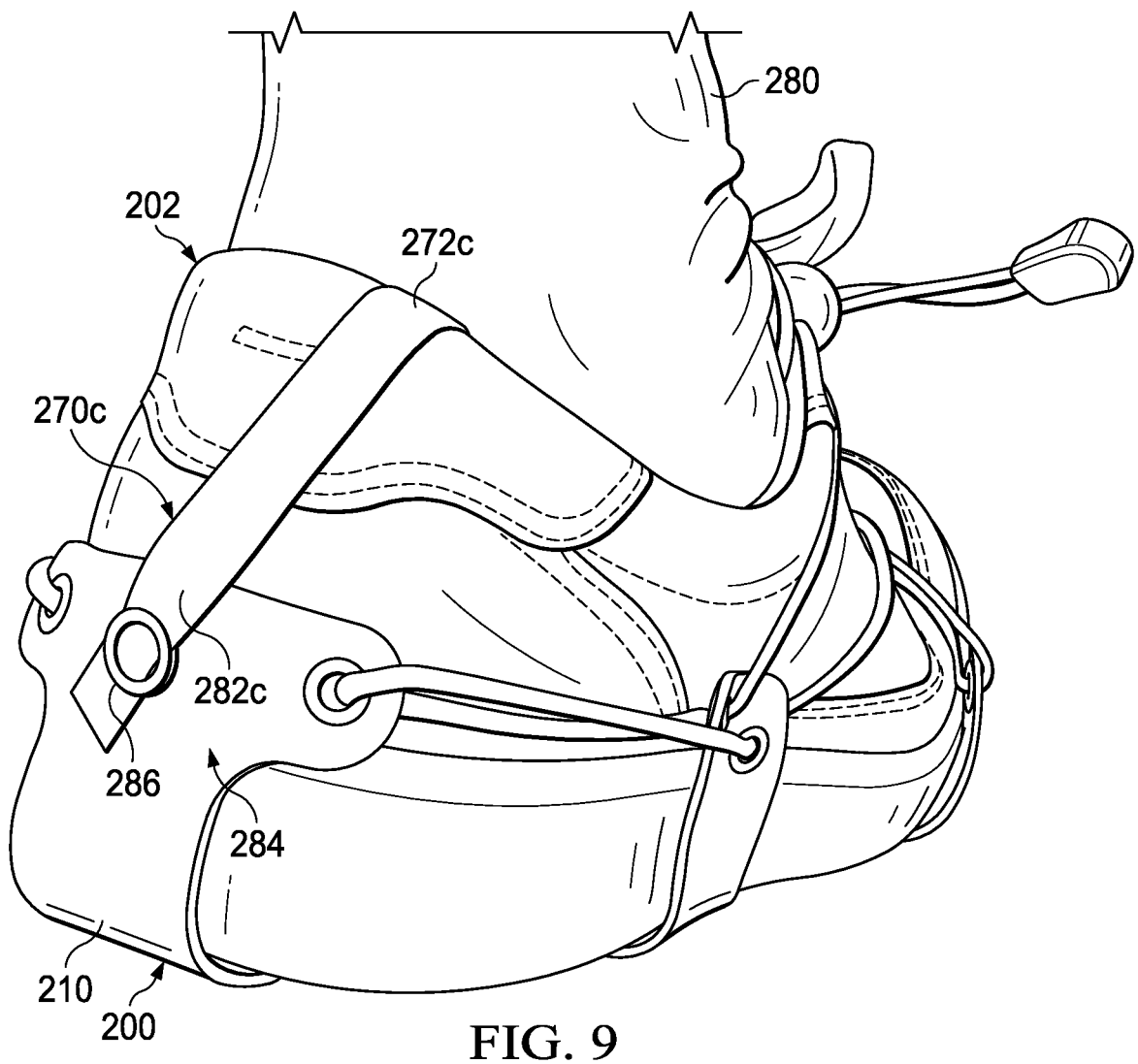
FIG. 9 depicts a conductive strand or strap placed within user's shoe, according to an embodiment.

At least a part of the electrical pathway or connection between user 203 and grounding device 200 may be provided by electrical conductors 270a, 270b, 270c, such as shown in FIGS. 7-9, for example. Electrical conductors 270a, 270b, 270c may be flexible and elongated in shape. In some embodiments, electrical conductors 270a, 270b, 270c may include a resistor (not shown) which may eliminate or reduce pain or injury to user 203 caused by a discharge of static electricity. One end of electrical conductors 270a, 270b, 270c may be connected to or in direct contact with the body of user 203 (e.g., by directly touching the user's skin or clothing fabric that is touching the skin) and a second end of electrical conductors 270a, 270b, 270c may be connected to any one or more of base 204, elongated portion 210, spacer portion 232, or any one or more wing of first and second pairs of wings 206, 208. When grounding device 200 is in contact with grounded surface 230, such as, for example, a grounded floor of a building or a grounded mat disposed on the building's floor, any static electrical charge that might otherwise build up or exist on user's body, may instead flow from user 203 through electrical conductors 270a, 270b, 270c, through grounding device 200 and to electrical ground via grounded surface 230.

Referring to FIG. 7, electrical conductor 270a has a first end 272a that is in electrical connection with user's 203 body via a detachable connection to an ECG electrode 274, which may be disposable and may be placed on or attached to user's skin, such as with an adhesive backing, for example. In an embodiment, an ECG electrode, which uses foam tape and has a 4 mm male snap, may be Red Dot™ part number 2560, manufactured by 3M Company. However other types of ECG electrodes or similar devices may be used as well.

In an alternative embodiment, as shown in FIG. 8, a first end 272b of electrical conductor 270b may be in electrical connection with user's 203 body via a band 276 or strap which may be placed in contact with and secured to the skin of user's leg by being worn about the leg, for example. In an embodiment, band 276 may be made of an elastic fabric for easily conforming to the user's leg and may include an electrically conductive material inserted within the band which touches the skin of the user's leg.

In yet another embodiment, as shown in FIG. 9, electrical conductor 270c may comprise a conductive strand or strap having a first end 272c which may be placed within user's shoe 202, so that an electric charge may flow from user's foot through conductive strap/electrical conductor 270c. To achieve this, conductive strap/electrical conductor 270c may be placed between the inside of shoe 202 and a sock 280 worn by user 203, or alternatively, may be placed inside both shoe 202 and sock 203, so that electrical conductor 270c may directly contact the skin of user's foot. According to an embodiment, electrical conductor 270c may be constructed of a fabric such as, for example, polyester, and may include a metallic thread or an electrically conductive elastomer. In other embodiments, however, other materials may be used that provide for flexibility, user comfort and electrical conductivity.

Electrical conductors 270a, 270b, 270c of FIGS. 7-9 have second ends 282a, 282b, 282c that may be detachably connected to grounding device 200. While FIGS. 7-9 illustrate an attachment location 284 for second ends 282a, 282b, 2082c that is disposed on elongated portion 210 of grounding device 200, other embodiments may include attachment locations disposed at other locations on grounding device 200. For example, such other attachment locations may include one or more locations on one or more wings of first and second pairs of wings 206, 208, or on other locations of grounding device 200, where these other locations may have the conductive properties generally described elsewhere herein.

In order to detachably connect second ends 282a, 282b, 282c of electrical conductors 270a, 270b, 270c, to grounding device 200 at attachment location 284, an electrically conductive, metal snap connector 286 may be used. However, other types of connectors may be used as well such as, for example, (a) a banana jack, (b) a polymer snap, (c) a buckle, (d) a D-ring, or (e) a snap hook. Such connectors may permit the electrical charge to flow from electrical conductors 270a, 270b, 270c, to base 204, elongated portion 210, or at least one wing of first and second pairs of wings 206, 208, or some other location of grounding device 200. As can be seen, the use of such connectors may advantageously provide users with an option to easily change the type of component for use in connecting to user's body without the necessity of locating and donning a different grounding device.

Although the above descriptions of FIGS. 7-9 are provided in relation to certain components in the illustrated embodiment of FIGS. 4-6, these descriptions may apply as well to the embodiments of FIGS. 1-3, and to other embodiments described herein.

Figure 10:
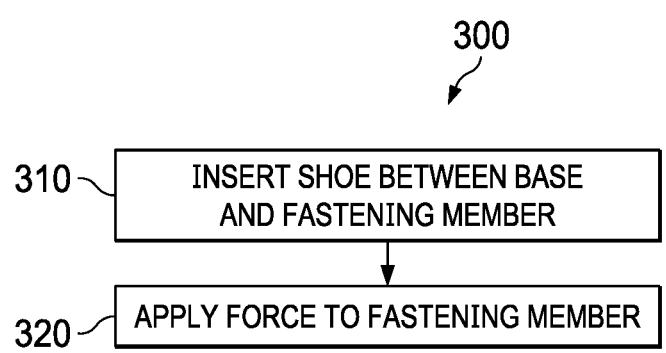
FIG. 10 is a simplified flow diagram of a method of using a grounding device, according to an embodiment.

FIG. 10 illustrates a simplified flow diagram of a method 300 of using a grounding device having a base, a pair of wings and an elongated portion. Examples of grounding devices that may be used with method 300 may include grounding device 100 and grounding device 200 described herein with reference to FIGS. 1-9, although other embodiments of grounding devices disclosed herein may be used in accordance with method 300 as well. At block 310, a user's shoe may be placed or inserted between a base and a fastening member. Fastening member may be elongated in shape and may be flexible. At least portions of pair of wings and elongated portion may be flexible. Pair of wings extends outwardly from base, and elongated portion extends from base in a direction generally perpendicular to pair of wings. At least one of base, elongated portion, or one wing of pair of wings may be in electrical communication with electrical ground, directly or indirectly, during a time that base is disposed between shoe and a grounded surface and that shoe is on grounded surface.

In an embodiment, fastening member may be constructed of an elastic material permitting an extension of the length of the fastening member in response to an external longitudinal force or a pulling force applied at or near one or more ends of fastening member (such as a force being applied by user, for example), and further permitting a retraction in the length of fastening member in response to a release of the pulling force. In an embodiment, fastening member may comprise a shock cord (sometimes also referred to as a bungee cord). In yet another embodiment, while fastening member may be flexible, it also may be non-elastic, thus not materially stretching or extending in length in response to a longitudinal or pulling force. In various embodiments, fastening member may comprise a strap, a strand, a rope, a lace, a cord, a string, a band, a ribbon, a wire, and/or a line. Moreover, fastening member may comprise a single, continuous member, and in alternative embodiments may comprise a plurality of members that may be cooperatively engaged with one another.

Fastening member may engage each wing of pair of wings and elongated portion at a plurality of engagement locations disposed on pair of wings and elongated portion. In an embodiment, plurality of engagement locations may be disposed so that, when shoe is placed between base and fastening member, fastening member may entwine grounding device and extend across a top portion of shoe and along the left side and right side of shoe and further may extend toward and loop back from the rear of shoe.

At block 320 of FIG. 10, a force may be applied to fastening member which may result in a flexing of pair of wings and elongated portion so as to grip shoe at locations on the left and right sides of shoe and on the rear portion of shoe. In an embodiment, such a force may comprise a single pull on or near one or both ends of fastening member, thereby simultaneously snugging or tightening the entirety of grounding device onto shoe. Moreover, in an embodiment, at least one of base, elongated portion, or one wing of pair of wings may have dimensions and may be constructed in whole or in part, of a flexible material (e.g., rubber or vinyl), so that a single grounding device may accommodate a range of shoe sizes and designs, thus reducing the size of an inventory of grounding devices that might otherwise be required by a plurality of persons working in the same location.

In an embodiment of the method of FIG. 10, a force may comprise a longitudinal or pulling force applied to fastening member, which in turn may be constructed of an elastic material. This material may permit an extension of the length of fastening member in response to the applied pulling force, and further may permit a retraction or reduction in the length of fastening member in response to a release of the pulling force. In an embodiment, fastening member may comprise a shock cord, and applying the force to fastening member may comprise pulling shock cord.

In an embodiment, the method further may comprise closing a clamping mechanism that is cooperatively engaged with fastening member, thereby retaining a force exerted by fastening member resulting from the pulling of it. In an embodiment, clamping mechanism may comprise a cord lock, although other clamping mechanisms may be used as well.

In yet another embodiment, the method further may comprise removably attaching one end of an electrical connector to base, or elongated portion or one wing of pair of wings. Electrical connector may be elongated in shape and may be flexible. In an embodiment, the method may further comprise attaching the other end of electrical conductor to an ECG electrode and attaching the ECG electrode to the user's skin. In alternative embodiments, however, the method may comprise attaching the other end of electrical conductor to a band or strap and attaching band or strap to the user's leg, such as, for example, by wrapping the band or strap around the leg. In an alternative embodiment, the other end may comprise a conductive strand or strap, and the method may further comprise placing at least a portion of strand or strap within the user's shoe such as, for example, placing it between the user's sock and shoe, or alternatively, between the user's foot and sock so that strand or strap may be directly in contact with the skin of the user.

In an embodiment of the method of FIG. 10, base, pair of wings and elongated portion may be formed together in a generally T shape. At least a portion of elongated portion may be in contact with a rear outsole portion of shoe when grounding device is attached to shoe. In an embodiment, base, elongated portion, and pair of wings all may be constructed of flexible rubber, at least portions of which may include laminated layers. The inside laminate layer (referring to the layer that is in direct contact with shoe) may include portions that may not be conductive to electricity, and the outside or opposite laminate layer may include portions that may be infused with carbon particles thereby making these portions conductive to electricity. However, the foregoing is only an example; other embodiments may include other constructions that provide material flexibility and further provide electrical conductivity to permit at least a portion of the electrical pathway described herein.

In an embodiment of the method of FIG. 10, a plurality of engagement locations may be disposed on pair of wings and on elongated portion, and a plurality of engagement mechanisms (for cooperatively engaging fastening member) may be disposed at plurality of engagement locations. In an embodiment, plurality of engagement mechanisms may comprise one or more of hooks or loops, or any combination thereof.

In an alternative embodiment of the method of FIG. 10, a plurality of openings may be defined by each wing of pair of wings and by elongated portion at plurality of engagement locations. Fastening member may engage pair of wings and elongated portion by entwining pair of wings and elongated portion and extending through plurality of openings. Referring again to block 320, the force applied to fastening member may comprise a pulling of fastening member.

In yet a further alternative embodiment of the method of FIG. 10, a second pair of wings may extend outwardly from base and may be spaced apart from first pair of wings, and a plurality of engagement locations may be disposed on both first and second pairs of wings, as well on other locations described above. A force applied to fastening member further may cause second pair of wings to grip left and right sides of shoe.

In an embodiment, a grounding device is provided which can be removably attached to a user's shoe. Grounding device may include a base that is shaped so that at least a portion of it may be disposed under the shoe when grounding device is attached. At least a portion of base may be constructed of a material that is electrically conductive so that base may be in electrical communication with a grounded surface when in contact with it. For example, embodiments may include base being constructed of a rubber material having electrically conductive properties, or alternatively, may be constructed of a flexible polymer material having electrically conductive properties.

In an embodiment, base may be constructed of flexible rubber, wherein at least portions of which may include laminated layers. The inside laminate layer (referring to the layer that is in direct contact with shoe) may include portions that are not conductive to electricity, and the outside or opposite laminate layer may include portions that may be infused with carbon particles thereby making these portions conductive to electricity. However, the foregoing is only an example; other embodiments may include other constructions that provide material flexibility and electrical conductivity to permit at least a portion of the electrical pathway described herein.

Base may be in cooperative engagement with a flexible fastening member at at least one engagement location on base. The at least one engagement location may be disposed on base so that fastening member, which may be generally elongated in shape, may engage base by entwining base and extending across a top portion of shoe and along left and right sides of shoe and further extending toward and looping back from a heel portion of shoe. In an embodiment, a plurality of openings defined by base may be disposed at a plurality of engagement locations. Fastening member may extend through plurality of openings for cooperative engagement with base. However, rather than a plurality of openings, alternative embodiments may include hooks, or loops, or any combination thereof, disposed on or connected to base at plurality of engagement locations and having a capability of cooperatively engaging or securing fastening member.

In an embodiment, base may be flexible thereby permitting it to grip shoe at locations on its left and right sides and on its heel portion in response to a force provided by fastening member, thus permitting grounding device to be removably attachable to shoe. On the other hand, when the force of fastening member is reduced or removed, base may relax or loosen its grip, thus permitting easy removal of grounding device from shoe.

In an embodiment, a single pull on or near one or both ends of fastening member may simultaneously snug or tighten the entirety of base onto shoe. Moreover, in an embodiment, base may have dimensions and may be constructed in whole or in part, of a flexible material (e.g., rubber or vinyl), so that a single grounding device may accommodate a range of shoe sizes and designs, thus reducing the size of an inventory of grounding devices that might otherwise be required for a plurality of persons working in the same location.

In an embodiment, fastening member may be constructed of an elastic material permitting an extension of the length of fastening member in response to an external longitudinal force or a pulling force applied at or near one or more ends of fastening member (such as a force being applied by the user, for example), and further permitting a retraction or reduction in the length of fastening member in response to a release of the pulling force. In an embodiment, fastening member may comprise a shock cord (sometimes also referred to as a bungee cord). In yet another embodiment, while fastening member may be flexible, it also may be non-elastic, thus not materially stretching or extending in length in response to the longitudinal or pulling force. In various embodiments, fastening member may comprise a strap, a strand, a rope, a lace, a cord, a string, a band, a ribbon, a wire, and/or a line. Moreover, fastening member may comprise a single, continuous member, or alternatively may comprise a plurality of members that may be attached to or cooperatively engaged with one another.

A clamping mechanism may secure fastening member on base while retaining a force of fastening member resulting from the pulling of fastening member. Clamping mechanism may receive the first and second ends of fastening member and may selectively permit fastening member to slide through the mechanism while clamping mechanism is in an unlocked or opened condition or to prevent movement through clamping mechanism when in a locked or closed condition. In an embodiment, clamping mechanism may comprise a cord lock. Cord locks may also be known as cord fasteners, plastic stoppers, spring clasps or cord toggles. In addition to cord locks, other types of clamping mechanisms for securing fastening member and retaining the force of fastening member may include cord stoppers, latches, magnetic clamps, and hose clamps.

An electrical pathway or connection between a user's body and base may be provided by an electrical conductor which may be flexible and elongated in shape. Electrical conductor may have one end attached to a user's body and a second end attached to base. Thus, while base is in contact with the grounded surface, such as, for example, a grounded floor of a building or a grounded mat disposed on the building's floor, any static electric charge that might otherwise remain on a user's body, may instead flow from the user's body through electrical conductor, through base (which is attached to user's shoe) and to grounded surface.

In an embodiment, a first end of electrical conductor may be attached to a user's body by use of an ECG electrode which may be placed on such a user's skin and attached to the first end of electrical conductor. In an alternative embodiment, the attachment may be achieved by a band or strap attached or strapped to a user's leg and further attached to first end of electrical conductor. In yet a further embodiment, the attachment may be achieved by a conductive strand or strap for placement within a user's shoe and attached to (or an integral part of) first end of electrical conductor. At least a portion of conductive strand may be placed between the shoe and a sock being worn by user, or may be placed inside of a user's sock (i.e., directly touching the skin of the user's foot) which in turn may be inside shoe. In an embodiment, conductive strap may be constructed of a fabric such as, for example, polyester, and may include a metallic thread or an electrically conductive elastomer. In other embodiments, however, other materials may be used that provide for flexibility, user comfort and electrical conductivity.

In an embodiment, attached to the second end of electrical conductor may be a connector that is electrically conductive and that may permit selectively connecting and disconnecting electrical conductor to base. Such connectors may include a banana jack, a polymer snap, a metal snap, a buckle, a D-ring, and a snap hook. Other types of connectors that permit the flow of electricity through them may be used as well.

The particular combinations of elements and features in the embodiments described herein are exemplary only; the interchanging and substitution of these teachings with other teachings in this and any incorporated-by-reference documents are also expressly contemplated and intended.

Terms such as "over", "under", "above" and "below" may be used to facilitate discussion, but are not intended to necessarily restrict scope of claimed subject matter. For example, the terms "over" and "above", as an example, are not meant to suggest that claim scope is limited to only situations in which an embodiment is right side up, such as in comparison with the embodiment being upside down, for example. An example includes an apparatus or assembly, as one illustration, in which, for example, orientation at various times (e.g., during fabrication) may not necessarily correspond to orientation of a final product. Thus, if an object, as an example, is within applicable claim scope in a particular orientation, such as upside down, as one example, likewise, it is intended that the latter also be interpreted to be included within applicable claim scope in another orientation, such as right side up, again, as an example, and vice-versa, even if applicable literal claim language has the potential to be interpreted otherwise. Of course, again, as always has been the case in the specification of a patent document, particular context of description and/or usage provides helpful guidance regarding reasonable inferences to be drawn.

Reference herein to a "shoe" is made for convenience and to simplify the description herein. However, the term "shoe" should be construed to include shoes of the type shown in the illustrated embodiments, as well as other types of shoes and/or footwear that may be worn by a user along with a grounding device.

Unless otherwise indicated, in the context of the present patent document, the terms "forward," "rear" (or "rearward"), "left," and "right" generally may be construed as follows when used in connection with features or components of a grounding device and/or a user's shoe: The term "forward" generally may be a reference to a location (or a relative position) that is generally proximate to the user's toes and/or generally distal from the user's heel in relation to other features or components, when the user is wearing a shoe and/or a grounding device. The terms "rear" or "rearward" generally may be a reference to a location (or relative position) that is generally proximate to the user's heel and/or generally distal from the user's toes in relation to other features or components, when the user is wearing a shoe and/or a grounding device. The term "right" may be a reference to a location (or relative position) that is generally proximate to the user's right side (e.g., the side having the user's right arm, right leg, right foot, etc.) and generally distal from the user's left side (e.g., the side having the user's left arm, left leg, left foot, etc.) in relation to other features or components, when the user is wearing a shoe and/or a grounding device. The term "left" may be a reference to a location (or relative position) that is generally proximate to the user's left side and generally distal from the user's right side in relation to other features or components, when the user is wearing a shoe and/or a grounding device.

Unless otherwise indicated, in the context of the present patent document the term "or" if used to associate a list, such as A, B, or C, is intended to mean A, B, and C, here used in the inclusive sense, as well as A, B, or C, here used in the exclusive sense. The term "and/or" can be used in an abundance of caution to make clear that all of the foregoing meanings are intended, although such usage is not required. In addition, the term "one or more" or similar terms is used to describe any feature, structure, characteristic, or the like in the singular. "And/or" is also used to describe a plurality or some other combination of features, structures, characteristics, or the like.

Unless expressly stated otherwise, the terms "connected" and "attached" as used herein are broad terms and are to be given their ordinary and customary meaning to a person of ordinary skill in the art (and is not to be limited to a special or customized meaning), and furthermore refers without limitation to both an indirect attachment between two or more parts, as well as a direct attachment between two or more parts.

As previously mentioned, unless specifically stated otherwise, it is appreciated that throughout this document the use of terms such as "first", "second", "third", etc., is a common patent-language convention to distinguish between repeated instances of an element or limitation. Unless the context clearly indicates otherwise, these terms are to distinguish different elements of an embodiment or claim, and are not terms intended to supply a numerical limit, and are not terms to indicate that elements, limitations or actions must appear or be performed in that order.

References throughout this document to one implementation, an implementation, one embodiment, an embodiment and/or the like means that a particular feature, structure, and/or characteristic described in connection with a particular implementation and/or embodiment is included in at least one implementation and/or embodiment of claimed subject matter. Thus, appearances of such phrases, for example, in various places throughout this specification are not necessarily intended to refer to the same implementation or to any one particular implementation described. Furthermore, it is to be understood that particular features, structures, and/or characteristics described are capable of being combined in various ways in one or more implementations and, therefore, are within intended claim scope, for example. In general, of course, these and other issues vary with context. Therefore, particular context of description and/or usage provides helpful guidance regarding inferences to be drawn.

In view of the above, it will be appreciated that certain embodiments of the invention overcome many of the long-standing problems in the art by providing electrostatic grounding devices and methods for use in dissipating static electricity that might otherwise build up on a user's body. Embodiments include grounding devices that may be easily attached to and removed from a user's shoe, and that may provide user comfort. Comfort may be provided by use of a covering material or base constructed of rubber, vinyl or other flexible material, which also may permit a single grounding device to be used for a variety of sizes and shapes of shoes. At least a portion of the flexible material is electrically conductive and in electrical communication with the user's skin via a variety of easily attachable/detachable, electrically-conductive attachment options for electrically connecting the grounding device to the user's body. The user may select any one or more of these attachment options without having to obtain a different grounding device base.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. A grounding device for removable attachment to a shoe of a user having a body including a foot having a heel, wherein the grounding device further is for dissipating static electricity from the body to a grounded surface, wherein the grounding device further is for use with an electrical conductor and a fastening member,
    wherein the shoe has a midsole and an outsole, and
        wherein the outsole of the shoe includes a rear outsole portion disposed generally under the heel of the foot during a time that the shoe is worn by the user,
    the grounding device comprising:
        a base shaped to fit under at least a portion of the outsole of the shoe, wherein at least a portion of the base is disposed between the at least the portion of the outsole of the shoe and the grounded surface during a time that the grounding device is attached to the shoe;
        a pair of wings extending outwardly from the base, wherein at least a portion of each wing of the pair of wings is positioned adjacent to the midsole of the shoe during the time that the grounding device is attached to the shoe; and
        an elongated portion extending from the base in a direction generally perpendicular to the pair of wings, wherein at least a portion of the elongated portion is in contact with the rear outsole portion of the outsole during the time that the grounding device is attached to the shoe,
    wherein the electrical conductor is elongated in shape and is flexible and is to provide at least part of an electrical pathway between the body and at least one of the base, the elongated portion, or at least one wing of the pair of wings, during a time that the electrical conductor connects the body to the grounding device,
    wherein the fastening member is elongated in shape and is flexible, wherein the fastening member engages each wing of the pair of wings and the elongated portion at a plurality of engagement locations disposed on the pair of wings and on the elongated portion during the time that the grounding device is attached to the shoe, and
    wherein at least portions of the pair of wings and of the elongated portion are flexible thereby permitting the pair of wings and the elongated portion to grip the shoe in response to a force provided by the fastening member during the time that the grounding device is attached to the shoe.

2. The grounding device of claim 1, wherein the grounding device further comprises the electrical conductor, and wherein the electrical conductor includes an electrically conductive connector for removably attaching the electrical conductor to at least one of the base, the elongated portion or at least one wing of the pair of wings.

3. The grounding device of claim 1, further comprising a plurality of engagement mechanisms disposed at the plurality of engagement locations, wherein the plurality of engagement mechanisms comprises one or more hooks or loops, or any combination thereof, and wherein the fastening member engages each wing of the pair of wings and the elongated portion by engaging the one or more hooks or loops, or any combination thereof.

4. The grounding device of claim 3, wherein the foot further has an arch, wherein the shoe has an upper comprising an upper right sidewall and an upper left sidewall, wherein the shoe further has a top portion extending generally over the arch of the foot during the time that the shoe is worn by the user, wherein the plurality of engagement mechanisms is disposed so that, during the time that the grounding device is attached to the shoe, the fastening member extends across the top portion of the shoe and along the upper left sidewall and the upper right sidewall of the shoe, and further extends toward the rear outsole portion of the shoe.

5. The grounding device of claim 1, wherein a plurality of openings is defined by each wing of the pair of wings and by the elongated portion at the plurality of engagement locations, wherein the fastening member engages the pair of wings and the elongated portion by extending through the plurality of openings, and wherein the force provided by the fastening member to grip the shoe is in response to a pulling force on the fastening member.

6. The grounding device of claim 5, wherein the fastening member comprises an elastic material permitting an extension of a length of the fastening member in response to the pulling force, and further permitting a retraction of the length of the fastening member in response to a release of the pulling force.

7. The grounding device of claim 5, wherein the fastening member comprises a shock cord.

8. The grounding device of claim 5, wherein the foot further has an arch, wherein the shoe has an upper comprising an upper right sidewall and an upper left sidewall, wherein the shoe further has a top portion extending generally over the arch of the foot during the time that the shoe is worn by the user, wherein the plurality of openings is disposed so that, during the time that the grounding device is attached to the shoe, the fastening member extends across the top portion of the shoe and along the upper left sidewall and the upper right sidewall of the shoe, and further extends toward the rear outsole portion of the shoe.

9. The grounding device of claim 5, wherein the midsole of the shoe has a right side and a left side, wherein the pair of wings comprises a right wing and a left wing, wherein the right wing and the left wing are disposed adjacent to the right and left sides, respectively, of the midsole during the time that the grounding device is attached to the shoe,
wherein the plurality of openings comprises a first opening, a second opening, a third opening, a fourth opening, a fifth opening, and a sixth opening, wherein the first opening and the second opening are defined by the right wing, the third opening and the fourth opening are defined by the left wing, and the fifth opening and the sixth opening are defined by the elongated portion,
wherein the fastening member extends through the plurality of openings in the following sequence: through the first opening of the right wing, the fifth opening of the elongated portion, the second opening of the right wing, the third opening of the left wing, the sixth opening of the elongated portion, and the fourth opening of the left wing.

10. The grounding device of claim 1, wherein the grounding device further is for use with a clamping mechanism, wherein the fastening member has a first end and a second end, wherein during the time that the grounding device is attached to the shoe, the first and second ends extend through the clamping mechanism, and wherein the clamping mechanism selectively permits the fastening member to slide through the clamping mechanism or to prevent movement through the clamping mechanism.

11. The grounding device of claim 10, wherein the fastening member comprises a shock cord, and wherein the clamping mechanism comprises a cord lock.

12. The grounding device of claim 1, wherein the base, the pair of wings and the elongated portion are formed together as a unitary body.

13. The grounding device of claim 1, wherein the base, the pair of wings and the elongated portion are formed together in a generally T-shape.

14. The grounding device of claim 1, wherein at least one of the base, the elongated portion, and one wing of the pair of wings comprises a flexible material having conductive properties.

15. The grounding device of claim 1, wherein the grounding device further comprises the fastening member, and wherein the fastening member comprises an elastic material permitting an extension of a length of the fastening member in response to a pulling force applied to the fastening member, and further permitting a retraction of the length of the fastening member in response to a release of the pulling force, and
wherein the force provided by the fastening member is in response to the pulling force.

16. The grounding device of claim 1, wherein the grounding device further comprises the fastening member, and wherein the fastening member is non-elastic.

17. The grounding device of claim 1, wherein the grounding device further is for use with an electrocardiogram (ECG) electrode for placement on skin of the user, and wherein the electrical conductor is in electrical connection with the body via the ECG electrode.

18. The grounding device of claim 1, wherein the body further includes a leg, wherein the grounding device further is for use with a band for placement on the leg, and wherein the electrical conductor is in electrical connection with the body via a connection with the band.

19. The grounding device of claim 1, wherein the electrical conductor comprises a conductive strand for placement within the shoe.

20. The grounding device of claim 1, wherein the electrical conductor includes an electrically conductive connector for removably attaching the electrical conductor to the base.

21. The grounding device of claim 20, wherein the electrically conductive connector comprises at least one of a banana jack, a polymer snap, a metal snap, a buckle, a D-ring, or a snap hook.

22. The grounding device of claim 1, wherein the pair of wings is a first pair of wings, and wherein the grounding device further comprises a second pair of wings extending outwardly from the base and spaced apart from the first pair of wings, wherein the plurality of engagement locations is further disposed on the second pair of wings,
wherein at least a portion of each wing of the second pair of wings is positioned adjacent to the midsole of the shoe during the time that the grounding device is attached to the shoe,
wherein the fastening member engages each wing of the second pair of wings at at least one of the plurality of engagement locations during the time that the grounding device is attached to the shoe, and
wherein at least a portion of the second pair of wings is flexible thereby permitting the second pair of wings to grip the shoe in response to the force provided by the fastening member during the time that the grounding device is attached to the shoe.

23. The grounding device of claim 22, wherein the grounding device further comprises the electrical conductor, and wherein the electrical conductor includes an electrically conductive connector for removably attaching the electrical conductor to at least one of the base, the elongated portion, or at least one wing of the first and second pairs of wings.

24. The grounding device of claim 22, wherein the grounding device further comprises the fastening member, and wherein the fastening member comprises an elastic material permitting an extension of a length of the fastening member in response to a pulling force applied to the fastening member, and further permitting a retraction of the length of the fastening member in response to a release of the pulling force, and
wherein the force provided by the fastening member is in response to the pulling force.

25. The grounding device of claim 22, wherein the grounding device further comprises the fastening member, and wherein the fastening member is non-elastic.

26. The grounding device of claim 22, wherein each pair of the first and second pairs of wings are angled away from one another, wherein one pair of the first and second pairs of wings is angled in a forward direction and the other pair of the first and second pairs of wings is angled in a rearward direction.

27. The grounding device of claim 22, wherein the foot includes an arch of the foot, wherein the outsole of the shoe further includes a middle outsole portion disposed generally under the arch of the foot during the time that the shoe is worn by the user, wherein the base includes a spacer portion disposed so that the second pair of wings is spaced apart from the first pair of wings by the spacer portion, and wherein the spacer portion is further disposed so that it generally is in contact with the middle outsole portion of the outsole of the shoe during the time that the grounding device is attached to the shoe.

28. The grounding device of claim 22, wherein the first and the second pairs of wings, the base, and the elongated portion are formed together as a unitary body.

29. The grounding device of claim 22, further comprising a plurality of engagement mechanisms disposed at the plurality of engagement locations, wherein the plurality of engagement mechanisms comprises one or more hooks or loops, or any combination thereof, and wherein the fastening member engages each wing of the first and second pairs of wings and the elongated portion by engaging the one or more hooks or loops, or any combination thereof.

30. The grounding device of claim 22, wherein the foot includes an arch of the foot, wherein the shoe has an upper comprising an upper right sidewall and an upper left sidewall, wherein the shoe further has a top portion extending generally over the arch of the foot during the time that the shoe is worn by the user, wherein the plurality of engagement locations is disposed so that, during the time that the grounding device is attached to the shoe, the fastening member extends across the top portion of the shoe and along the upper left sidewall of the shoe and the upper right sidewall of the shoe and further extends toward the rear outsole portion of the shoe.

31. The grounding device of claim 22, wherein a plurality of openings is defined by each wing of the first and second pairs of wings and by the elongated portion, and wherein the fastening member engages the first and second pairs of wings and the elongated portion by extending through the plurality of openings, and wherein the force provided by the fastening member to grip the shoe is in response to a pulling force on the fastening member.

32. The grounding device of claim 31, wherein the fastening member comprises an elastic material permitting an extension of a length of the fastening member in response to the pulling force applied to the fastening member, and further permitting a retraction of the length of the fastening member in response to a release of the pulling force.

33. The grounding device of claim 31, wherein the midsole of the shoe has a right side and a left side, wherein the first pair of wings is disposed between the elongated portion of the grounding device and the second pair of wings, wherein the first pair of wings comprises a right first wing and a left first wing, wherein the right first wing and the left first wing are disposed adjacent to the right and left sides, respectively, of the midsole during the time that the grounding device is attached to the shoe, wherein the second pair of wings comprises a right second wing and a left second wing, wherein the right second wing and the left second wing are disposed adjacent to the right side of the midsole and the left side of the midsole, respectively, of the shoe during the time that the grounding device is attached to the shoe, wherein the plurality of openings comprises a first opening, a second opening, a third opening, a fourth opening, a fifth opening, a sixth opening, a seventh opening, and an eighth opening, wherein the first opening and the second opening are defined by the right first wing, the third opening and the fourth opening are defined by the left first wing, the fifth opening is defined by the right second wing, the sixth opening is defined by the left second wing, and the seventh opening and the eighth opening are defined by the elongated portion, wherein the fastening member extends through the plurality of openings in the following sequence: through the first opening of the right first wing, the seventh opening of the elongated portion, the second opening of the right first wing, the sixth opening of the left second wing, the fifth opening of the right second wing, the fourth opening of the left first wing, the eighth opening of the elongated portion, and the third opening of the left first wing.

34. A method of using a grounding device having a base, a pair of wings, and an elongated portion, the method comprising:

placing a shoe of a user between the base and a fastening member, wherein the fastening member is elongated in shape and is flexible, and wherein at least portions of the pair of wings and the elongated portion are flexible, wherein at least one of the base, the elongated portion, or at least one wing of the pair of wings is in electrical communication with ground during a time that the base is disposed between the shoe and a grounded surface and that the shoe is on the grounded surface, wherein the pair of wings extends outwardly from the base, wherein the elongated portion extends from the base in a direction generally perpendicular to the pair of wings, wherein the fastening member engages each wing of the pair of wings and the elongated portion at a plurality of engagement locations disposed on the pair of wings and on the elongated portion, wherein the plurality of engagement locations is disposed so that, during the time that the shoe is disposed between the base and the fastening member, the fastening member extends across a top portion of the shoe and along a left side of the shoe and a right side of the shoe and further extends in directions toward and away from a rear portion of the shoe; and applying a force to the fastening member thereby causing the pair of wings and the elongated portion to grip the shoe at locations on the left side of the shoe and the right side of the shoe and on the rear portion of the shoe.

35. The method of claim 34, wherein the fastening member comprises an elastic material permitting an extension of a length of the fastening member in response to a pulling force applied to the fastening member, and further permitting a retraction of the length of the fastening member in response to a release of the pulling force, and wherein the applying the force to the fastening member comprises applying the pulling force to the fastening member.

36. The method of claim 34, wherein the fastening member comprises a shock cord, and wherein the applying the force to the fastening member comprises pulling the shock cord.

37. The method of claim 35, further comprising closing a clamping mechanism cooperatively engaged with the fastening member thereby retaining a holding force on the fastening member resulting from the pulling force.

38. The method of claim 37, wherein the clamping mechanism comprises a cord lock.

39. The method of claim 34 further comprising removably attaching one end of an electrical conductor to one wing of the pair of wings, or to the elongated portion, or to the base, wherein the electrical conductor is elongated in shape and is flexible.

40. The method of claim 39, further comprising attaching another end of the electrical conductor to an electrocardiogram (ECG) electrode; and attaching the ECG electrode to the user.

41. The method of claim 39, further comprising attaching another end of the electrical conductor to a band; and attaching the band to a leg of the user.

42. The method of claim 39, wherein the electrical conductor comprises a conductive strand, and wherein the method further comprises placing at least a portion of the conductive strand within the shoe.

43. The method of claim 34, wherein a plurality of engagement mechanisms is disposed at the plurality of engagement locations, wherein the plurality of engagement mechanisms comprises one or more hooks or loops, or any combination thereof, and wherein cooperative engagement of the fastening member with the pair of wings and the elongated portion comprises an engagement with the one or more hooks or loops, or any combination thereof.

44. The method of claim 34, wherein a plurality of openings is defined by each wing of the pair of wings and by the elongated portion at the plurality of engagement locations, wherein the fastening member engages the pair of wings and the elongated portion by extending through the plurality of openings, and wherein the applying the force to the fastening member comprises pulling the fastening member.

45. The method of claim 34, wherein the base, the pair of wings and the elongated portion are formed together in a generally T-shape.

46. The method of claim 34, wherein the pair of wings is a first pair of wings, and wherein a second pair of wings extends outwardly from the base and is spaced apart from the first pair of wings,
  wherein at least one of the plurality of engagement locations is disposed on the second pair of wings, and
  wherein the applying of the force to the fastener member further causes the second pair of wings to grip the shoe on the left side of the shoe and on the right side of the shoe.

* * * * *